United States Patent [19]

Duffy

[11] 3,980,786

[45] Sept. 14, 1976

[54] 1,3-DIHYDRO-3-PHENYL-1'-(2-PROPYNYL)SPIRO[ISOBENZOFURAN]S

[75] Inventor: Brian J. Duffy, Flanders, N.J.

[73] Assignee: American Hoechst Corporation, Bridgewater, N.J.

[22] Filed: July 15, 1975

[21] Appl. No.: 596,163

[52] U.S. Cl. .......................... 424/267; 260/293.58; 260/326.5 D; 260/346.2 R; 424/274; 424/285
[51] Int. Cl.² ........................................ C07D 405/04
[58] Field of Search ............... 260/293.58, 326.5 D, 260/346.2 R; 424/267, 274, 285

[56] References Cited

UNITED STATES PATENTS

| 3,635,956 | 1/1972 | Krapcho | 260/240 K |
|---|---|---|---|
| 3,686,186 | 8/1972 | Houlihan | 260/293.58 |

*Primary Examiner*—G. Thomas Todd
*Attorney, Agent, or Firm*—Curtis, Morris & Safford

[57] ABSTRACT

Novel 1,3-dihydro-3-phenyl-1'-(2-propynyl)spiro[isobenzofuran]s and methods of preparing the same are described. These compounds are useful as antidepressants.

15 Claims, No Drawings

1,3-DIHYDRO-3-PHENYL-1'-(2-PROPYNYL)-SPIRO[ISOBENZOFURAN]S

This invention relates to novel 1,3-dihydro-3-phenyl-1'-(2-propynyl)spiro[isobenzofuran]s and pharmaceutically acceptable salts thereof which are useful as antidepressants, to a method of preparing the same, to a method of treatment of depression with pharmaceutically effective amounts thereof, and to pharmaceutical compositions containing such compounds as essential active ingredients.

To the best of my knowledge, the compounds of this invention have not heretofore been described or suggested. Spiro[phthalan-piperidine]s described by W. J. Houlihan et al. in U.S. Pat. No. 3,686,186, 1,3-dihydrospiro[isobenzofuran]s described by Bauer and Kosley in U.S. Pat. application Ser. No. 424,080 filed Dec. 12, 1973 and substituted 1,3-dihydrospiro[isobenzofuran]s described by Bauer and Kosley in U.S. Pat. application Ser. No. 502,650 filed Sept. 3, 1974 are outside the scope of this invention. The same applies to the natural product of the formula

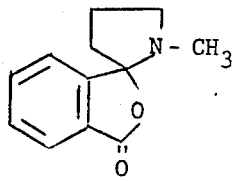

described by Y. Inushubi et al. [Chem. and Pharm. Bull. (Japan), 12, 749 (1964)].

The compounds of this invention are significantly different from the compounds of the prior art and exhibit unanticipatedly good pharmacological activity and low toxicity levels.

This invention relates to novel 1,3-dihydro-3-phenyl-1'-(2-propynyl)spiro[isobenzofuran]s of the formula

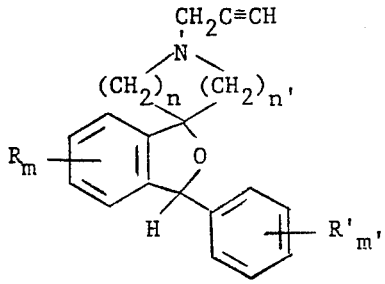

wherein R and R' are lower alkyl, lower alkoxy, halogen or hydroxy; $m$ and $m'$ are the integers 1 or 2; $n$ and $n'$ are integers from 1 to 3 with the sum of $n$ and $n'$ being 3, 4 or 5; and the pharmaceutically acceptable acid addition salts thereof. The terms "lower alkyl" and "lower alkoxy" are intended to include alkyl and alkoxy of 1 to 6 carbon atoms.

Acids useful for preparing the pharmaceutically acceptable acid addition salts of this invention include inorganic acids such as hydrochloric, hydrobromic, sulfuric, nitric, phosphoric and perchloric, as well as organic acids such as tartaric, citric, acetic, succinic, maleic, fumaric and oxalic acids.

The compounds of the present invention are prepared by the addition of a propargyl halide, preferably propargyl chloride, to a 1,3-dihydro-3-phenyl-spiro[isobenzofuran-cycloazalkane] of the formula

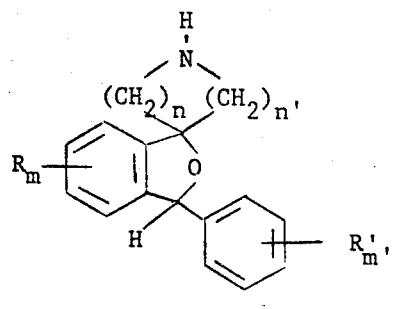

in the presence of an organic solvent and an acid scavenger at a temperature from ambient to the reflux point of the reaction mixture. The 1,3-dihydro-3-phenyl-spiro[isobenzofuran]s starting materials are described in U.S. application Ser. No. 502,650, cited above. In preferred method, n-butanol is utilized as the solvent and potassium carbonate as the acid scavenger at a temperature just below reflux.

Compounds of the present invention are useful in the treatment of depression in mammals, as demonstrated by their ability to inhibit tetrabenazine-induced depression in mice [International Journal of Neuropharmacology, 8, 73 (1969)], a standard assay for useful antidepressant properties. Thus, for example, 1,3-dihydro-3-phenyl-1'-(2-propynyl)spiro[isobenzofuran-1,4'-piperidine] effects a 50% inhibition of ptosis of tetrabenazine-induced depression at the intraperitoneal dose of 1.3 mg/kg of body weight. This datum indicates that compounds of the present invention are useful in treatment of depression in mammals when administered in amounts ranging from 1 to about 50 mg per kg of body weight per day.

Compounds of the present invention exhibit low toxicity levels. For example, the $ALD_{50}$ (acute lethal intraperitoneal dose, mg/kg of body weight, in 50% of the mice tested) for 1,3-dihydro-3-phenyl-1'-(2-propynyl)-spiro[isobenzofuran-1,4'-piperidine] is 562 mg/kg. This datum was generated by testing groups of four mice at various doses and noting the number of deaths.

Illustrative examples of compounds of the invention are:

1,3-dihydro-6-fluoro-3-phenyl-1'-(2-propynyl)-spiro[isobenzofuran-1,4'-piperidine];

1,3-dihydro-6-fluoro-3-(4-fluorophenyl)-1'-(2-propynyl)spiro[isobenzofuran-1,4'-piperidine];

1,3-dihydro-3-(3,4-dimethoxyphenyl)-1'-(2-propynyl)spiro[isobenzofuran-1,4'-piperidine];

1,3-dihydro-3-(4-hydroxyphenyl)-1'-(2-propynyl)-spiro[isobenzofuran-1,4'-piperidine];

1,2',3,3',4',5',6',7'-octahydro-3-phenyl-1'-(2-propynyl)spiro[isobenzofuran-1,4'-azepine];

1,3-dihydro-5-propoxy-3-phenyl-1'-(2-propynyl)-spiro[isobenzofuran-1,4'-piperidine];

1,3-dihydro-3-(4-ethylphenyl)-1'-(2-propynyl)-spiro[isobenzofuran-1,4'-piperidine]; and 1,3-dihydro-6-isopropyl-3-phenyl-1'-(2-propynyl)-spiro[isobenzofuran-1,4'-piperidine].

Effective quantities of the compounds of the invention may be administered to a patient by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches, and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such at magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent, and certain preservatives, dyes and colorings, and flavors. Materials used in preparing these various compositions should be pharmaceutically pure and non-toxic in the amounts used.

For the purpose of parenteral therapeutic administration, the active compounds of the invention may be incorporated into solutions or suspensions. These preparations should contain at least 0.1% of active compound, but this may be varied to be between 0.5 and about 30% of the weight thereof. The amount of active compound in such compositions is such that an effective dosage will be obtained. Preferred compositions and preparations according to the present invention are prepared so that parenteral dosage units contain between 0.5 to 100 milligrams of active compound.

The solutions or suspensions may also include the following components: sterile diluents such as water for injection, saline solutions, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparations can be enclosed in ampules, disposable syringes or multiple dose vials made of glass or plastic.

EXAMPLE 1.0 ml of propargyl chloride is added to a solution of 3.0 g of 1,3-dihydro-3-phenylspiro[isobenzofuran-1,4'-piperidine] and 10.0 g of potassium carbonate in 100 ml of n-butanol. The mixture is heated with stirring almost to the reflux point of the solution (about 115°C.) where it is maintained for 26 hours. The mixture is filtered at 90°C. to remove inorganic salts and the filtrate upon cooling yields crystals which are removed by filtration, washed with n-butanol, and recrystallized from ethanol to give colorless needles, mp 146°–147°C., of 1,3-dihydro-4-phenyl-1'-(2-propynyl)-spiro[isobenzofuran-1,4'-piperidine].
Analysis:
Calculated for $C_{21}H_{21}NO$: 83.13%C; 6.98%H; 4.62%N.
Found: 83.01%C; 7.12%H; 4.51%N.

In analogous manner 1,3-dihydro-3-phenyl-spiro[isobenzofuran-1,3'-pyrrolidine], 1,3-dihydro-3-phenylspiro[isobenzofuran-1,3'-piperidine], 1,3-dihydro-6-methoxy-3-phenylspiro[isobenzofuran-1,4'-piperidine], 1,3-dihydro3-(4-tolyl)spiro[isobenzofuran-1,4'-piperidine], 1,3-dihydro6-hydroxy-3-phenyl-spiro[isobenzofuran-1,4'-piperidine], 1,3-dihydro-5-hydroxy-3-phenylspiro[isobenzofuran-1,4'-piperidine] and 1,3-dihydro-3-(4-fluorophenyl)spiro[isobenzofuran-1,4'-piperidine] are treated to provide 1,3-dihydro-3-phenyl-1'-(2-propynyl)spiro[isobenzofuran-1,3'-pyrrolidine], 1,3-dihydro-3-phenyl-1'-(2-propynyl)-spiro[isobenzofuran-1,3'-piperidine], 1,3-dihydro-6-methoxy-3-phenyl-1'-(2-propynyl)-spiro[isobenzofuran-1,4'-piperidine], 1,3-dihydro-1'-(2-propynyl)-3-(4-tolyl)spiro[isobenzofuran-1,4'-piperidine], 1,3-dihydro-6-hydroxy-3-phenyl-1'-(2-propynyl)-spiro[isobenzofuran-1,4'-piperidine], 1,3-dihydro-5-hydroxy-3-phenyl-1'-(2-propynyl)spiro[isobenzofuran-1,4'-piperidine] and 1,3-dihydro-3-(4-fluorophenyl)-1'-(2-propynyl)spiro[isobenzofuran-1,4'-piperidine], respectively.

I claim:
1. A compound of the formula

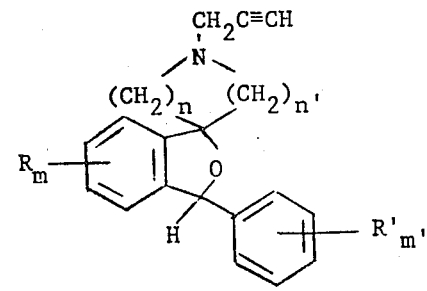

wherein R and R' are lower alkyl, lower alkoxy, halogen, hydroxy; m and m' are the integers 0, 1 or 2; n and n' are integers from 1 to 3 with the sum of n and n' being 3, 4 or 5; and the pharmaceutically acceptable acid addition salts thereof.

2. A compound as defined in claim 1 wherein m and m' are 0 or 1.

3. A compound as defined in claim 1 wherein R and R' are alkyl of from 1 to 3 carbon atoms, alkoxy of 1 to 4 carbon atoms, halogen, or hydroxy.

4. A compound as defined in claim 3 wherein m and m' are 0 or 1, and n and n' are integers from 1 to 3 with the sum of n and n' being 3 or 4.

5. A compound as defined in claim 1 wherein R and R' are methyl, methoxy, chlorine, fluorine or hydroxy, $m$ and $m'$ are 0 or 1 and $n$ and $n'$ are integers from 1 to 3 with the sum of $n$ and $n'$ being 3 or 4.

6. A compound as defined in claim 5 wherein the sum of $n$ and $n'$ is 4.

7. The compound defined in claim 1 which is 1,3-dihydro-3-phenyl-1'-(2-propynyl)spiro[isobenzofuran-1,4'-piperidine].

8. The compound defined in claim 1 which is 1,3-dihydro-3-phenyl-1'-(2-propynyl)spiro[isobenzofuran-1,3'-pyrrolidine].

9. The compound defined in claim 1 which is 1,3-dihydro-3-phenyl-1'-(2-propynyl)spiro[isobenzofuran-1,3'-piperidine].

10. The compound defined in claim 1 which is 1.3dihydro-6-hydroxy-3-phenyl-1'-(2-propynyl)-spiro[isobenzofuran-1,4'-piperidine].

11. The compound defined in claim 1 which is 1,3-dihydro-5-hydroxy-3-phenyl-1'-(2-propynyl)-spiro[isobenzofuran-1,4'-piperidine].

12. The compound defined in claim 1 which is 1,3dihydro-3-(4-hydroxyphenyl)-1'-(2-propynyl)-spiro[isobenzofuran-1,4'-piperidine].

13. The compound defined in claim 1 which is 1,3-dihydro-3-(4fluorophenyl)-1'-(2-propynyl)-spiro[isobenzofuran-1,4'-piperidine].

14. A method of treating depression which comprises administering to a patient a pharmaceutically effective amount of a compound defined in claim 1.

15. A pharmaceutical composition which comprises between about 0.5 and 70 percent by weight of a compound defined in claim 1 as an active ingredient, the balance being a pharmaceutically acceptable carrier therefor.

* * * * *